(12) United States Patent
den Boer et al.

(10) Patent No.: US 6,301,506 B1
(45) Date of Patent: Oct. 9, 2001

(54) TECHNIQUES OF TREATING PATIENTS WITH ELECTROMAGNETIC RADIATION

(75) Inventors: Willem Maurits Johannes den Boer, Rozendaal (NL); Johannes Adrianus Valk, Chazelles Charente (FR)

(73) Assignee: Raitec B.V. (NL)

( * ) Notice: Subject to any disclaimer, the term of this patent is extended or adjusted under 35 U.S.C. 154(b) by 0 days.

(21) Appl. No.: 09/345,117

(22) Filed: Jul. 6, 1999

(30) Foreign Application Priority Data

Jul. 6, 1998 (NL) .................................................. 1009568

(51) Int. Cl.$^7$ ....................................................... A61F 2/00
(52) U.S. Cl. ............................ 607/100; 607/115; 607/62; 600/26
(58) Field of Search .............................. 607/100, 45, 61, 607/62, 96, 101, 115, 144, 145, 149; 600/26, 27, 28, 9

(56) References Cited

U.S. PATENT DOCUMENTS 5,634,939 * 6/1997 Kuster et al. ........................... 607/59

* cited by examiner

Primary Examiner—Linda C. M. Dvorak
Assistant Examiner—R. Kearney
(74) Attorney, Agent, or Firm—Michaelson & Wallace; Peter L. Michaelson

(57) ABSTRACT

An electromagnetic apparatus for treating patients. The apparatus comprises an electromagnetic frequency generator and a coil connected thereto for transmitting electromagnetic energy to a body part of a patient. A control connects to the electromagnetic frequency generator and to a number of sensors that register a local skin temperature and/or a skin resistance of the body part. The control contains an algorithm comprising an adjustment module and a treatment module. The adjustment module causes the transmission of electromagnetic energy of different test frequencies while recording with respect to each of the test frequencies corresponding variations observed by the sensors. The adjustment module is further arranged for determining a treatment frequency at which a significant variation is observed with at least one of the sensors. The treatment module implements a treatment schedule that includes transmitting electromagnetic energy to the body part at the treatment frequency during predetermined treatment periods and with a predetermined treatment amplitude.

20 Claims, 6 Drawing Sheets

Measurement window

Patient data
- Patient ID:
- Sensitivity class: 1
- Treatment no.: 1

Signal definition
- Freq. (Hz): 100
- Ampl. (mV): 150
- Wave form: Square / Sine

Dose definition
- Signal duration (s): 1
- Repeats/sites (s): 1
- Interval time (s): 1
- Sites: R L Signal: Toe L, instep L, heel L, toe R, instep R, heel R
Note:

Temperature (°C): 18.0–38.0
Time: 0–3

Status: END | Save | Stop meeting | Start

FIG. 5

TECHNIQUES OF TREATING PATIENTS WITH ELECTROMAGNETIC RADIATION

BACKGROUND OF THE INVENTION (1) Field of the Invention

This invention relates to techniques of treating patients with electromagnetic radiation via an apparatus comprising a frequency generator and a coil connected thereto for transmitting electromagnetic waves. The apparatus further comprises a control provided with at least one output that connects to the frequency generator.

(2) Description of Related Art

Such an apparatus is disclosed, for instance, in Dutch patent application NL-A-7501352. The known apparatus is intended for treating patients with electromagnetic radiation. In this known apparatus, use is made of electromagnetic waves of a frequency in the range of substantially 0–1,000 Hz, and more particularly in the range of 600–800 Hz. The field intensity of the electromagnetic waves is not described in this publication. The coils used in the known apparatus are particularly large and defy handling. Moreover, the influence of the varying electromagnetic field on a patient is not determined in any way. With the known apparatus, there is total objective uncertainty as to whether any effect is achieved. Only from the patient's subjective findings can it be inferred if any wholesome effect has occurred.

An apparatus of the type described in the preamble is also disclosed in Dutch patent application NL-A-8503057. That known apparatus is intended in particular to promote the restoration of bone fractures. To that end, an electromagnetic signal with a very specific curve and pattern is proposed.

An apparatus as described in the preamble is also used in the practice of a physiotherapist. The frequencies and powers of the electromagnetic waves used are such as to internally induce a local heating of a tissue, essentially in the manner of a microwave oven.

BRIEF SUMMARY OF THE INVENTION

An object of the present invention is to provide an apparatus that influences the autonomic nervous system. The field intensities and/or the frequencies of the electromagnetic waves employed in the present technique lie in a different range than in the above-described prior art apparatuses. Moreover, the frequencies activated to influence an autonomic nervous system will in general differ for each patient.

According to the invention, the apparatus of the type set forth in the preamble is characterized in that the apparatus further comprises a number of sensors for registering the local temperature and/or skin resistance of the body. The control is provided with at least one input to which the sensors are connectable. In addition, the control is provided with an algorithm comprising an adjustment module, which is arranged for transmitting electromagnetic waves of different test frequencies, and for recording, with respect to each test frequency, variations observed by the sensors. In addition, the adjustment module is further arranged to determine a frequency of the electromagnetic waves, referred to as a treatment frequency, at which a significant variation is observed with at least one of the sensors.

The temperature sensors are placed, for instance, on the instep, the heel and the big toe. Skin resistance sensors are preferably placed on standard meridian points such as are known from acupuncture. The coil is held, for instance, near the sole of the foot, and the algorithm of the control is started. At the first treatment, after patient data have been made known to the computer, the treating person starts the adjustment module. The control controls the frequency generator, such that a number of short pulses of electromagnetic waves are given at intervals of, for instance, four minutes, while the frequency of the electromagnetic waves of the successive pulses increases by increments of 10 Hz. Thus, for instance, in a period of about 30 minutes, seven pulses can be given, starting with a frequency of, for instance, 100 Hz, and ending with a frequency of 160 Hz. While traversing the adjustment process, which is intended for determining the correct treatment frequency, the values measured by the sensors are stored in a memory of the control. At the end of the adjustment process, the control determines, on the basis of the measured and recorded temperature and/or skin resistance values, at what frequency a significant variation was observed by at least one of the sensors. That frequency, the so-called treatment frequency, can be used for the further treatment of the patient. This treatment frequency is generally different for each patient and is in line with the autonomic nervous system of the patient in question. The electromagnetic waves stimulate the autonomic nervous system when the correct treatment frequency is used. For a large number of syndromes, this has been found to have a beneficial effect. Various experiments have shown highly satisfactory results, inter alia in:

post-traumatic dystrophy;

ME;

fibromyalgia;

peripheral blood supply disturbances such as claudication, atherosclerosis, arthritis, gangrene and cold feet;

some forms of rheumatism;

disorders of a degenerative nature;

narcolepsy; and

UV-itis (rheumatic eye disorder).

According to a further feature of the invention, the apparatus may further be characterized in that the algorithm includes a treatment module for implementing a treatment schedule, comprising the transmission of electromagnetic waves of the determined treatment frequency during certain treatment periods and with a certain treatment amplitude.

After a correct treatment frequency has been determined by means of the adjustment module, it is possible—with the same apparatus if it has the above-described treatment module and optionally with a separate treatment apparatus comprising the same parts as the apparatus according to the invention, with the exception of the adjustment module described—to treat the patient in a number of successive treatment sessions with the treatment frequency as determined. The treating person can then hold the coil, for instance, at about 0.5–2 cm from the sole of the left and right feet alternately. During the treatment, a number of pulses of electromagnetic waves of the determined treatment frequency are administered. The sum duration of the signal that is given during a treatment session is between 15 and 60 seconds. The length of the pulses, the power of the electromagnetic waves, and the number of pulses administered per treatment session are preferably preprogrammed in the memory of the control and effected automatically by the algorithm in the treatment module. It is noted that the amount of energy that is administered via electromagnetic waves during a treatment session is particularly small. It would make a bicycle rear lamp burn only for a very short time. The patient's body itself provides the energy for initiating better blood supply and stimulating the functioning of the various organs. It is supposed that all of this is initiated by stimulation of the autonomic nervous system through the electromagnetic waves administered with an apparatus according to the invention.

Although most patients do not feel the signal, the effects that may already occur very shortly afterwards are in most cases clearly perceptible. During the treatments, the patients may observe the following:

- a strong increase in the temperature of limbs suffering from poor blood circulation;
- an initial severe hurt in limbs that were inactive for a prolonged time period;
- an activation in parts of the body or organs (kidneys, intestines);
- a clear diminish in pain;
- a very light tingling or pulsating sensation arising a few minutes after a pulse;
- a slight pressure in the head; and
- a tired or very languid sensation with a tendency to yawn.

According to a further embodiment of the invention, during the adjustment process, the frequency at which the sum of variations observed by all of the sensors is maximal can be selected as the treatment frequency.

Further embodiments of the invention are also described in detail with reference to the drawings.

BRIEF DESCRIPTION OF THE SEVERAL VIEWS OF THE DRAWINGS

FIG. 5 shows a Measurement Window display of control 3 of FIG. 1; and

DETAILED DESCRIPTION OF THE INVENTION

Figure 1:
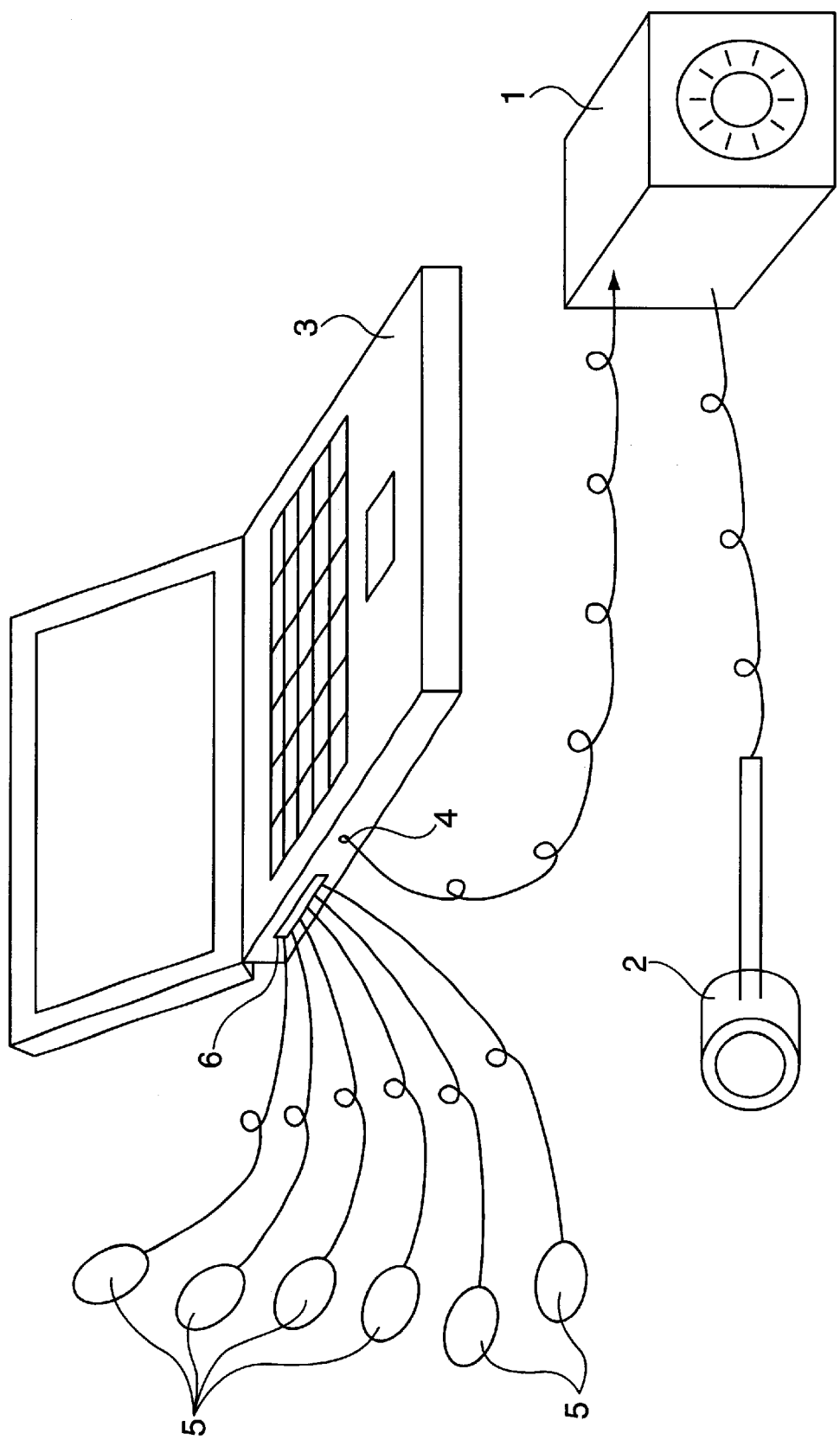
FIG. 1 shows a schematic representation of an exemplary embodiment of the apparatus according to the invention.

The exemplary embodiment of an apparatus according to the invention represented in FIG. 1 comprises frequency generator 1 and coil 2 connected thereto for transmitting electromagnetic waves. The apparatus further comprises control 3 which is provided with at least one output 4 which connects to frequency generator 1. The apparatus further comprises a number of temperature sensors 5 for registering the local temperature of a body part, for instance the temperature of a heel, an instep and a big toe on both feet. Needless to say, temperatures of other parts of a body, for instance, of the hands, can also be measured. Optionally, skin resistance sensors can also be used, which may be fitted at known acupuncture meridian points. Control 3 comprises at least one input 6 to which the temperature sensors 5 are connectable. In the present exemplary embodiment, control 3 is designed as a laptop computer. Control 3 is provided with an algorithm that comprises an adjustment module. The adjustment module is arranged for transmitting electromagnetic waves of different test frequencies and for recording, with respect to each test frequency, temperature variations observe by temperature sensors 5.

Figure 6:
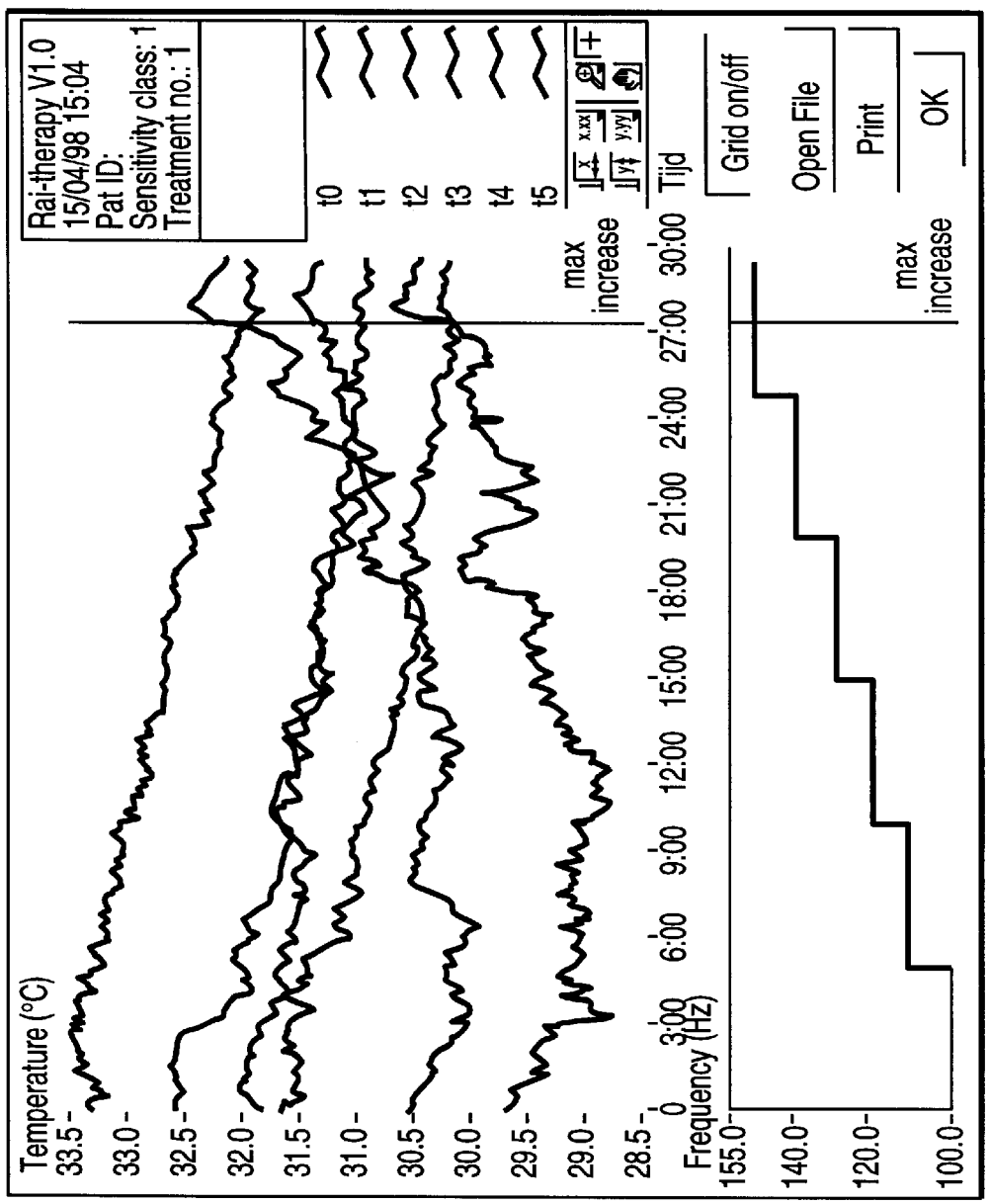
FIG. 6 shows a graphical display of control 3 of FIG. 1, illustrating a series of possible measurements made during an adjustment process.

FIG. 6 shows the course of the temperature changes observed by the different temperature sensors 5 under the influence of different pulses of electromagnetic waves of different frequencies. It is clear to see that after about 27 minutes of measurements, the instantaneous summed rises of the different temperatures sensed by all six sensors 5 had its maximal value, which is indicated by a vertical line drawn there. The frequency of the pulse preceding this maximal value point, optionally after making a small correction, is chosen as the so-called treatment frequency with which the patient will be treated in further treatment sessions.

Figure 2:
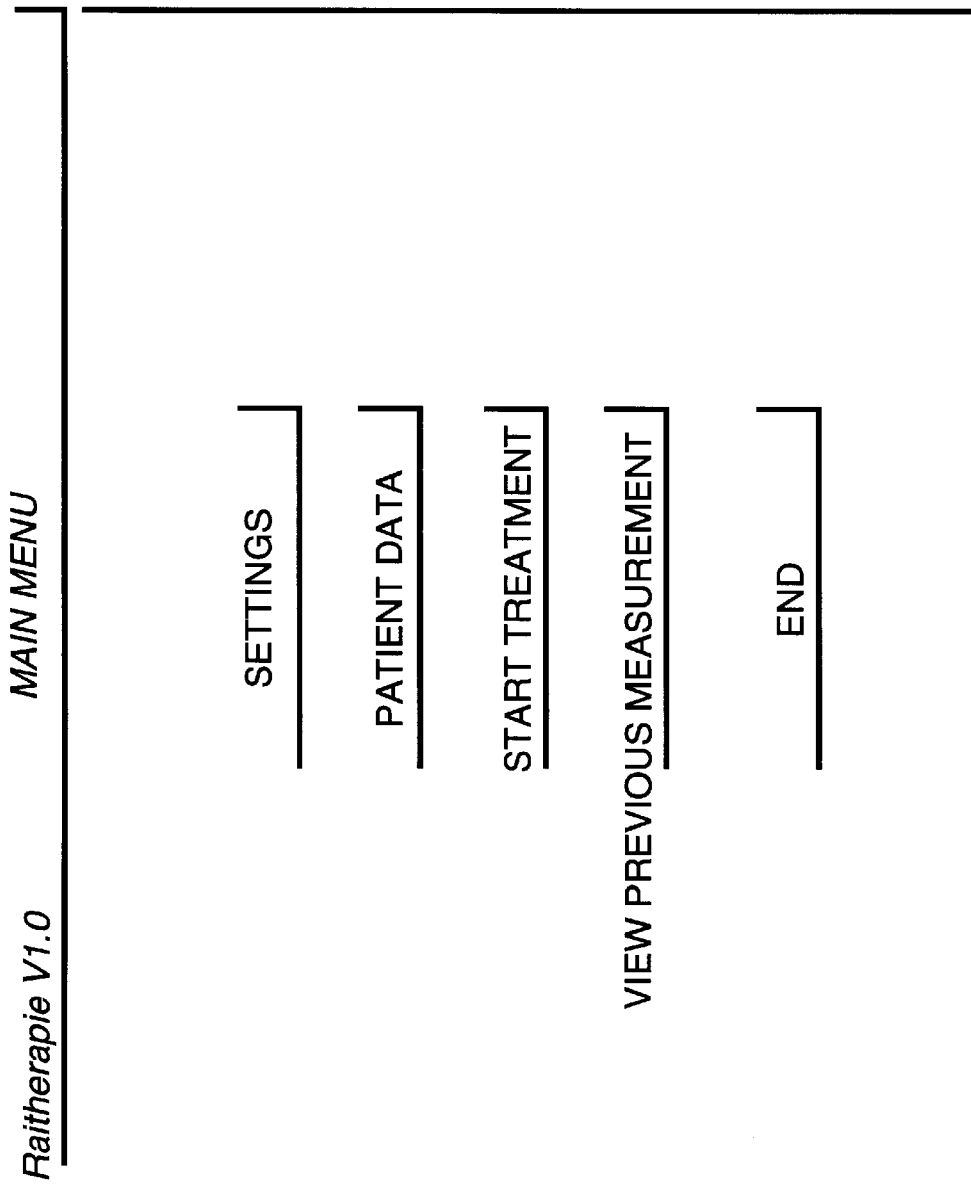
FIG. 2 shows a Main Menu display of control 3 of FIG. 1.

The algorithm of control 3 of the present exemplary embodiment can present a number of displays to the treating person. The starting display is represented in FIG. 2 and forms an access menu for the other parts of the algorithm.

Figure 3:
FIG. 3 shows a Settings display of control 3 of FIG. 1.

For the purpose of the further treatment sessions, the algorithm includes a treatment module for implementing a treatment schedule. The treatment schedule describes, inter alia, the different treatment periods and the associated treatment amplitudes of a particular treatment session. The treatment frequency for a patient is already fixed in that the adjustment process has been traversed. With the display represented in FIG. 3, different treatment schedules can be fixed.

Figure 4:
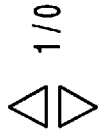
FIG. 4 shows a Patient Data display of control 3 of FIG. 1.

With the aid of the display shown in FIG. 4, the patient data can be inputted and, in addition, a certain treatment schedule can be assigned to a patient.

FIG. 5 shows a display presented by an algorithm during a treatment session. In this scheme, a number of relevant data items of a treatment is represented. In addition, the course of the temperature, as measured by the different temperature sensors 5 during a treatment session, can be accurately monitored.

It will be clear that the invention is not limited to the exemplary embodiment described above. Thus, many variations are conceivable for the displays to be presented by an algorithm. Optionally, between the coil 2 and the frequency generator 1, a signal amplifier may be included. The electromagnetic waves transmitted by coil 2 can be of the harmonic, square or saw-tooth type. Optionally, in determining the treatment frequency, an adjustment module can transmit, instead of electromagnetic waves, sound waves of similar frequencies. To that end, the frequency generator would be connected to a source of sound energy.

What is claimed is:

1. An apparatus for applying electromagnetic energy to a body part comprising:
   - a generator means for generating said electromagnetic energy at a plurality of different frequencies;
   - a coil means connected to said generator means for transmitting said electromagnetic energy to said body part;
   - a control connected to said generator means;
   - a sensor means connected to said control for sensing a local skin temperature or a local skin resistance of said body part; and
   - an algorithm resident in said control, said algorithm comprising an adjustment module means for:
      - causing said coil means to transmit electromagnetic energy at different test frequencies,
      - recording with respect to each of said different test frequencies corresponding variations in said local skin temperature and/or said local skin resistance sensed by said sensor means, and
      - establishing a treatment frequency for said body part as a function of said different test frequencies and a corresponding significant variation of said local skin temperature and/or said local skin resistance.

2. The apparatus of claim 1, wherein said algorithm further comprises a treatment module means for implementing a treatment schedule and causing said coil means to transmit said electromagnetic energy with a predetermined treatment amplitude at said treatment frequency during predetermined treatment periods.

3. The apparatus of claim 2, wherein said treatment module means implements said treatment schedule such that said coil means transmits said electromagnetic energy only at said treatment frequency and varies a duration period of transmission and a corresponding power level of said electromagnetic energy.

4. The apparatus of claim 1, wherein said coil means transmits said electromagnetic energy to said body part with a transmission power in a range of substantially 3 to 20 milliwatts.

5. The apparatus of claim 1, wherein said adjustment module means successively transmits, for short periods of a few seconds each, electromagnetic energy at each of said different test frequencies, said different test frequencies being in a range of substantially 30 to 300 Hz, preferably in the range of substantially 100 to 160 Hz.

6. The apparatus of claim 5, wherein said adjustment module means causes said coil means to transmit a series of spaced pulses of said electromagnetic energy at said different test frequencies, wherein the frequencies of successive ones of said spaced pulses differ by substantially 10 Hz, and wherein said pulses are spaced by at least one minute, and preferably by substantially four minutes.

7. The apparatus of claim 1, wherein said adjustment module means establishes said treatment frequency to be equal to that test frequency at which a corresponding sum of said variations sensed by said sensors has a maximal value.

8. The apparatus of claim 1, wherein said treatment module means causes said coil means to transmit said electromagnetic energy as harmonic waves.

9. The apparatus of claim 1, wherein said treatment module means causes said coil means to transmit said electromagnetic energy as square waves.

10. The apparatus of claim 1, wherein said treatment module means causes said coil means to transmit said electromagnetic energy as saw-tooth waves.

11. A method of applying electromagnetic energy to a body part comprising the steps of:

generating said electromagnetic energy at a plurality of different frequencies;

sensing a local skin temperature or a local skin resistance of said body part;

illuminating said body part with electromagnetic energy at different test frequencies;

recording with respect to each of said different test frequencies corresponding variations in said local skin temperature or said local skin resistance; and establishing a treatment frequency for said body part, said treatment frequency being a function of a significant one of said variations in said local skin temperature or said local skin resistance and a corresponding one of said different test frequencies.

12. The method of claim 11, further including illuminating said body part with electromagnetic energy at said treatment frequency during predetermined treatment periods and with predetermined treatment amplitudes.

13. The method of claim 12, wherein the step of transmitting said electromagnetic energy during predetermined treatment periods and with predetermined treatment amplitudes includes transmitting said electromagnetic energy with a transmission power in the range of substantially 3 to 20 milliwatts.

14. The method of claim 12, wherein the step of illuminating said body part with electromagnetic energy at said treatment frequency includes transmitting said electromagnetic energy only at said treatment frequency while varying a duration of transmission and a corresponding power level of said electromagnetic energy.

15. The method of claim 11, wherein the step of illuminating said body part with electromagnetic energy at different test frequencies includes successively transmitting, for short periods of a few seconds each, electromagnetic energy at each of said different test frequencies, said different test frequencies being in the range of 30 to 300 Hz, and preferably in the range of substantially 100 to 160 Hz.

16. The method of claim 15, wherein the step of illuminating said body part with electromagnetic energy at different test frequencies includes transmitting a series of spaced pulses of said electromagnetic energy at said different test frequencies, varying the frequencies of successive ones of said spaced pulses by substantially 10 Hz, and spacing said pulses by at least one minute, and preferably by substantially four minutes.

17. The method of claim 11, wherein the step of establishing a treatment frequency for said body part includes establishing said treatment frequency to be equal to that test frequency at which a corresponding sum of said variations in said local skin temperature or said local skin resistance has a maximal value.

18. The method of claim 11, wherein the step of illuminating said body part with electromagnetic energy at different test frequencies includes transmitting said electromagnetic energy as harmonic waves.

19. The method of claim 11, wherein the step of illuminating said body part with electromagnetic energy at said different test frequencies includes transmitting said electromagnetic energy as square waves.

20. The method of claim 14, wherein the step of illuminating said body part with electromagnetic energy at said different test frequencies includes transmitting said electromagnetic energy as saw-tooth waves.

* * * * *